United States Patent
Suzuki et al.

(10) Patent No.: US 10,258,694 B2
(45) Date of Patent: Apr. 16, 2019

(54) SKIN EXTERNAL PREPARATION AND SKIN IRRITATION-REDUCING METHOD

(71) Applicant: Shimadzu Corporation, Kyoto-shi (JP)

(72) Inventors: Kenichi Suzuki, Fuji (JP); Haruki Nakagawa, Fuji (JP); Yoshihiro Yamakita, Fuji (JP); Eiichi Ozeki, Kyoto (JP); Takashi Kawabe, Kyoto (JP); Eri Matsutani, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 0 days.

(21) Appl. No.: 15/312,985

(22) PCT Filed: May 21, 2015

(86) PCT No.: PCT/JP2015/064622
§ 371 (c)(1),
(2) Date: Nov. 21, 2016

(87) PCT Pub. No.: WO2015/178454
PCT Pub. Date: Nov. 26, 2015

(65) Prior Publication Data
US 2017/0151335 A1    Jun. 1, 2017

(30) Foreign Application Priority Data

May 23, 2014 (JP) ................................. 2014-107070

(51) Int. Cl.
| | |
|---|---|
| *A61K 47/34* | (2017.01) |
| *A61K 9/107* | (2006.01) |
| *A61K 9/50* | (2006.01) |
| *A61K 31/47* | (2006.01) |
| *A61K 9/00* | (2006.01) |
| *A61K 31/13* | (2006.01) |
| *A61K 31/325* | (2006.01) |
| *C08G 63/91* | (2006.01) |

(52) U.S. Cl.
CPC ............ *A61K 47/34* (2013.01); *A61K 9/0014* (2013.01); *A61K 9/107* (2013.01); *A61K 9/1075* (2013.01); *A61K 9/50* (2013.01); *A61K 31/13* (2013.01); *A61K 31/325* (2013.01); *A61K 31/47* (2013.01); *C08G 63/912* (2013.01); *C08G 2230/00* (2013.01)

(58) Field of Classification Search
None
See application file for complete search history.

(56) References Cited

U.S. PATENT DOCUMENTS

| | | | |
|---|---|---|---|
| 2008/0019908 | A1 | 1/2008 | Akitsu et al. |
| 2009/0232855 | A1 | 9/2009 | Kwon et al. |
| 2011/0104056 | A1 | 5/2011 | Hara et al. |

FOREIGN PATENT DOCUMENTS

| | | |
|---|---|---|
| EP | 2 305 214 A1 | 4/2011 |
| EP | 2 725 053 A1 | 4/2014 |
| JP | 2002-308728 A | 10/2002 |
| JP | 2008-24816 A | 2/2008 |
| JP | 2010-180145 A | 8/2010 |
| WO | 2009/148121 A1 | 12/2009 |

OTHER PUBLICATIONS

International Search Report dated Aug. 25, 2015 in PCT/JP15/064622 Filed May 21, 2015.
Akira Makino, et al., "Size Control of Core-Shell-type Polymeric Micelle with a Nanometer Precision" Langmuir, vol. 30, No. 2, Jan. 21, 2014, pp. 669-674 with cover page.
Office Action dated Oct. 18, 2018 in corresponding European Patent Application No. EP 15795860.4, filed May 21, 2015, 8 pages.

*Primary Examiner* — James W Rogers
(74) *Attorney, Agent, or Firm* — Oblon, McClelland, Maier & Neustadt, L.L.P.

(57) ABSTRACT

Provided is a skin external preparation including a drug and nanometer-size molecular assemblies. The molecular assemblies contain an amphiphilic block copolymer having a hydrophilic block chain including a sarcosine-derived structural unit and a hydrophobic block chain including a hydroxy acid-derived structural unit. The skin external preparation according to the present invention may reduce skin irritation caused by the drug, be very safe, and have excellent pharmacological effects, even when a drug that is generally difficult to be transdermally administered due to its strong skin irritation is contained therein.

11 Claims, 7 Drawing Sheets

SKIN EXTERNAL PREPARATION AND SKIN IRRITATION-REDUCING METHOD

TECHNICAL FIELD

The present invention relates to a skin external preparation. Further, the present invention relates to a skin irritation-reducing agent that can be used in combination with a skin external preparation to reduce skin irritation.

BACKGROUND ART

As conventional drug delivery systems or molecular imaging probes for labeling specific body tissues, various polymer nano-particles have been reported which carry, encapsulate, or bind with drugs or fluorescent dyes.

For example, Patent Document 1 discloses, as a drug delivery system or molecular imaging probe intended to be directly intravenously administered, an amphiphilic block polymer having a hydrophilic polypeptide chain including 10 or more sarcosine units and a hydrophobic molecular chain including 5 or more amino acid units or hydroxy acid units as essential structural units.

Further, Patent Document 2 discloses, as a molecular imaging probe intended to be directly intravenously administered, a molecular assembly containing two polymers, one of which is an amphiphilic block polymer having a hydrophilic block chain including 20 or more sarcosine units and a hydrophobic block chain including 10 or more lactic acid units and the other is a labeled polymer having at least 10 or more lactic acid units and a labeling group.

Meanwhile, for the purpose of enhancing the activity of a bioactive component in the skin, a transdermal external preparation has been proposed which includes polymethyl methacrylate (PMMA) nano-particles encapsulating a bioactive component (Patent Document 3). As in the case of this transdermal external preparation, for the purpose of allowing a bioactive component to act in the skin, a transdermal external preparation has also been proposed which includes PLGA nano-particles encapsulating tranexamic acid (Patent Document 4).

However, when the external preparation disclosed in Patent Document 3 is repeatedly used as a drug or cosmetic for a long time, there is a fear that PMMA remaining in the skin has adverse effects because PMMA is not a biodegradable polymer material. Further, there is a possibility that when the size of the particles is reduced, it is difficult to encapsulate a drug in the particles.

In the case of the external preparation disclosed in Patent Document 4, the amount of tranexamic acid that can be encapsulated in the PLGA nano-particles is very small, and therefore it is necessary to administer a large amount of the preparation in order to deliver tranexamic acid to a layer deeper than the skin layer (dermis). Further, when a drug that causes skin irritation is used, there is a fear that the drug that is too much to be encapsulated in the drug carrier has adverse effects on the skin.

PRIOR ART DOCUMENTS

Patent Documents

Patent Document 1: JP 2008-024816 A
Patent Document 2: WO 2009/148121 A
Patent Document 3: JP 2002-308728 A
Patent Document 4: JP 2010-180145 A

SUMMARY OF THE INVENTION

Problems to be Solved by the Invention

It is an object of the present invention to provide a skin external preparation that, even when a drug that is difficult to be transdermally administered due to its strong skin irritation is contained therein, reduces skin irritation caused by the drug, is very safe, and has excellent pharmacological effects.

Means for Solving the Problems

In order to achieve the above object, the present inventors have intensively studied, and, as a result, have found that the combined use of nanometer-size molecular assemblies containing a specific amphiphilic block copolymer and a drug makes it possible to obtain a skin external preparation that, even when a drug that is difficult to be transdermally administered due to its strong skin irritation is contained therein, reduces skin irritation caused by the drug, is very safe, and has excellent pharmacological effects. This finding has led to the completion of the present invention.

More specifically, the present invention provides a skin external preparation including a drug and nanometer-size molecular assemblies, wherein the molecular assemblies contain an amphiphilic block copolymer having a hydrophilic block chain including a structural unit derived from sarcosine and a hydrophobic block chain including a structural unit derived from hydroxy acid (hereinafter, this amphiphilic block copolymer is also simply referred to as "amphiphilic block copolymer").

The present invention also provides a skin irritation-reducing agent used for reducing skin irritation caused by a drug contained in a skin external preparation. The skin irritation-reducing agent including an amphiphilic block copolymer having a hydrophilic block chain including a structural unit derived from sarcosine and a hydrophobic block chain including a structural unit derived from hydroxy acid, the amphiphilic block copolymer being used for forming nanometer-size molecular assemblies.

Effects of the Invention

According to the present invention, it is possible to provide a skin external preparation that, even when a drug that is difficult to be transdermally administered due to its strong skin irritation is contained therein, reduces skin irritation caused by the drug, is very safe, and has excellent pharmacological effects. The skin external preparation according to the present invention also has high skin permeability.

BRIEF DESCRIPTION OF THE DRAWINGS

FIG. 4-1 is a graph showing the amount of total cholesterol after application of a skin external preparation.
FIG. 4-2 is a graph showing the amount of HDL cholesterol after application of a skin external preparation.

FIG. 4-3 is a graph showing the amount of LDL cholesterol after application of a skin external preparation.

FIG. 4-4 is a graph showing the amount of phospholipid after application of a skin external preparation.

FIG. 7-1 is a graph showing the results of an irritation test for rivastigmine with the use of a three-dimensional skin model.

FIG. 7-2 is a graph showing the results of an irritation test for rivastigmine with the use of a three-dimensional skin model.

MODE FOR CARRYING OUT THE INVENTION

Figure 1:
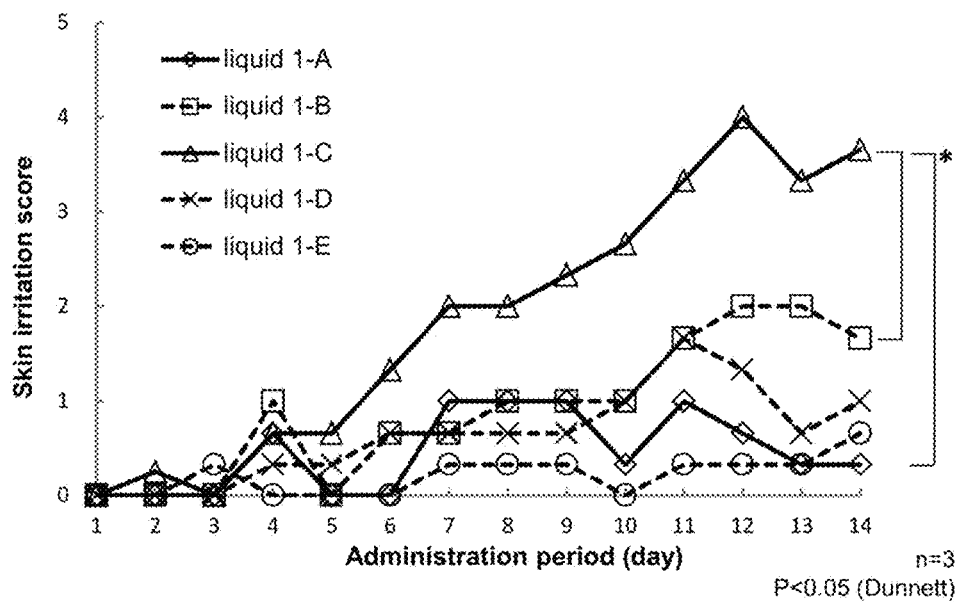
FIG. 1 is a graph showing the results of a skin irritation test for pitavastatin.

A skin external preparation according to the present invention includes: a drug; and nanometer-size molecular assemblies. The molecular assemblies contain an amphiphilic block copolymer having a hydrophilic block chain that has a structural unit derived from sarcosine and a hydrophobic block chain that has a structural unit derived from hydroxy acid.

<(A-1) Amphiphilic Block Copolymer>

(Hydrophilic Block Chain)

The hydrophilic block chain contained in the amphiphilic block copolymer has a structural unit derived from sarcosine. This structural unit improves hydrophilicity and flexibility of the hydrophilic block chain. The sarcosine-derived structural units contained in the hydrophilic block chain may all be continuous or may be discontinuous.

In this specification, the "hydrophilic block chain" refers to a block chain having hydrophilicity relatively higher than that of the hydrophobic block chain contained in the amphiphilic block copolymer and having such hydrophilicity that allows the amphiphilic block copolymer to self-assemble in a solvent to form self-assemblies (preferably, particulate self-assemblies).

From the viewpoint of skin irritation reduction, skin permeability, and pharmacological effects or from the viewpoint of easily controlling the molecular assemblies to have an appropriate size and a specific shape such as a micelle or vesicle, the hydrophilic block chain preferably has 20 or more sarcosine-derived structural units. The number of the sarcosine-derived structural units is more preferably 30 or more, further preferably 40 or more, and is preferably 500 or less, more preferably 200 or less, further preferably 150 or less, particularly preferably 100 or less.

Specifically, the sarcosine-derived structural unit is represented by the following chemical formula (1).

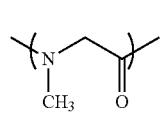

(1)

The amount of the sarcosine-derived structural unit contained in the hydrophilic block chain is preferably 50 to 100 mol %, more preferably 65 to 100 mol %, further preferably 80 to 100 mol %, particularly preferably 90 to 100 mol %.

Although the hydrophilic block chain may contain a sugar chain or a polyether chain, it is preferably a polypeptide chain. Besides the sarcosine-derived structural unit, examples of a structural unit contained in the hydrophilic block chain include structural units derived from amino acids other than sarcosine (including hydrophilic amino acids and other amino acids).

In this specification, the "amino acids" may be in any of L-form, D-form, and DL-form, and include natural amino acids, unnatural amino acids, and their derivatives obtained by modification and/or chemical modification and also include α-, β-, and γ-amino acids.

Among the above amino acids, hydrophilic amino acids are preferred. Specific examples thereof include serine, threonine, lysine, aspartic acid, and glutamic acid.

(Hydrophobic Block Chain)

The hydrophobic block chain contained in the amphiphilic block copolymer has a structural unit derived from hydroxy acid. The hydroxy acid-derived structural units contained in the hydrophobic block chain may all be continuous or may be discontinuous.

In this specification, the "hydrophobic block chain" refers to a block chain having hydrophobicity relatively higher than that of the hydrophilic block chain contained in the amphiphilic block copolymer and having such hydrophobicity that allows the amphiphilic block polymer to self-assemble in a solvent to form self-assemblies (preferably, particulate self-assemblies).

From the viewpoint of skin irritation reduction, skin permeability, and pharmacological effects or from the viewpoint of easily controlling the molecular assemblies to have an appropriate size and a specific shape such as a micelle or vesicle, the hydrophobic block chain preferably has 10 or more hydroxy acid-derived structural units. The number of the hydroxy acid-derived structural units is more preferably 15 or more, further preferably 20 or more, and is preferably 100 or less, more preferably 80 or less, further preferably 60 or less, particularly preferably 50 or less.

The hydroxy acid is preferably an aliphatic hydroxy acid. Examples of the aliphatic hydroxy acid include lactic acid, glycolic acid, and hydroxyisobutyric acid. These aliphatic hydroxy acids may be used singly or in combination of two or more of them.

Among them, lactic acid is particularly preferred from the viewpoint of improving solubility in low-boiling-point solvents, biocompatibility, and stability. The lactic acid may be any of L-lactic acid, D-lactic acid, and DL-lactic acid, and the hydrophobic block chain may include one of them alone or two or more of them.

A preferred specific example of the hydroxy acid-derived structural unit is represented by the chemical following chemical formula (2):

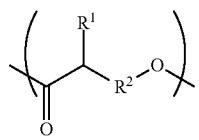

(2)

[In the chemical formula (2), R1 is a hydrogen atom or a methyl group and R2 is a single bond or a methylene group].

In the chemical formula (2), a combination of R1 and R2 is preferably a combination of a hydrogen atom or a methyl group as R1 and a single bond as R2 or a combination of a methyl group as R1 and a methylene group as R2, and is particularly preferably a combination of a methyl group as R1 and a single bond as R2, from the viewpoint of improving solubility in low-boiling-point solvents, biocompatibility, and stability.

The amount of the hydroxy acid-derived structural unit contained in the hydrophobic block chain is preferably 50 to 100 mol %, more preferably 65 to 100 mol %, further preferably 80 to 100 mol %, particularly preferably 90 to 100 mol %.

Examples of a structural unit, other than the hydroxy acid-derived structural unit, contained in the hydrophobic block chain include structural units derived from amino acids (including hydrophobic amino acids and other amino acids).

Many of hydrophobic amino acids have an aliphatic side chain, an aromatic side chain, or the like. Examples of a natural hydrophobic amino acid include alanine, valine, leucine, isoleucine, proline, methionine, and tryptophan. Examples of an unnatural hydrophobic amino acid derivative include methyl glutamate, benzyl glutamate, methyl aspartate, ethyl aspartate, and benzyl aspartate.

From the viewpoint of skin irritation reduction, skin permeability, and pharmacological effects, the ratio between the hydrophilic block chain and the hydrophobic block chain contained in the amphiphilic block copolymer used in the present invention [hydrophilic block chain:hydrophobic block chain] in terms of the number of structural units is preferably 10:1 to 1:1, more preferably 6:1 to 1.5:1, particularly preferably 5:1 to 1.6:1.

A preferred specific example of the amphiphilic block copolymer used in the present invention is represented by the following chemical formula (3):

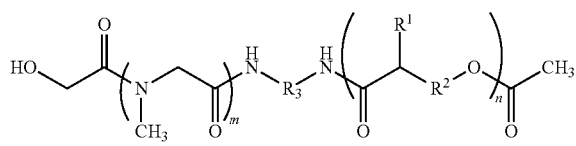

(3)

[In the chemical formula (3), R3 is a divalent hydrocarbon group having 1 to 6 carbon atoms, m is an integer of 20 to 200, n is an integer of 10 to 100, and R1 and R2 are the same as described above].

In the chemical formula (3), the divalent hydrocarbon group represented as R3 is preferably an alkylene group. The alkylene group may be either linear or branched. Specific examples of the alkylene group include a methylene group, an ethylene group, a trimethylene group, a propylene group (propane-1,2-diyl group), a tetramethylene group, a pentamethylene group, and a hexamethylene group.

The divalent hydrocarbon group preferably has 2 to 5 carbon atoms, more preferably 2 or 3 carbon atoms, further preferably 2 carbon atoms.

m is an integer of 20 to 200, preferably an integer of 30 to 150, more preferably an integer of 40 to 100. n is an integer of 10 to 100, preferably an integer of 15 to 80, more preferably an integer of 20 to 60, particularly preferably an integer of 20 to 50.

n R1s may be the same or different, and n R2s may also be the same or different.

Although the number-average molecular weight (Mn) of the amphiphilic block copolymer used in the present invention is not particularly limited, it is preferably 3,000 to 14,000, more preferably 3,000 to 9,000. Although the weight-average molecular weight (Mw) of the amphiphilic block copolymer is not particularly limited, it is preferably 3,000 to 14,000, more preferably 3,000 to 9,000.

The molecular weight distribution (Mw/Mn) of the amphiphilic block copolymer is preferably 1.5 or less.

The content amount of each of the structural units may be measured by $^{13}$C-NMR, $^1$H-NMR, or the like.

<(A-2) Hydrophobic Polymer>

The molecular assemblies used in the present invention may contain a hydrophobic polymer in addition to the amphiphilic block copolymer.

The above-described hydrophobic polymer (hereinafter, also simply referred to as a hydrophobic polymer) preferably has a structural unit derived from hydroxy acid from the viewpoint of biocompatibility, stability, and biodegradability or from the viewpoint of solubility in low-boiling-point solvents.

When the hydrophobic polymer has a hydroxy acid-derived structural unit, the number of the hydroxy acid-derived structural units is preferably 10 or more, more preferably 15 or more, further preferably 20 or more, and is preferably 200 or less, more preferably 160 or less, further preferably 100 or less from the viewpoint of affinity for the amphiphilic block polymer and from the viewpoint of easily controlling the molecular assemblies to have a shape such as a micelle or vesicle or an appropriate size.

It is preferred that the number does not exceed twice the number of structural units contained in the hydrophobic block chain of the amphiphilic block polymer.

The hydroxy acid is preferably an aliphatic hydroxy acid. Examples of the aliphatic hydroxy acid include lactic acid, glycolic acid, and hydroxyisobutyric acid. These aliphatic hydroxy acids may be used singly or in combination of two or more of them.

Among them, lactic acid is particularly preferred from the viewpoint of improving solubility in low-boiling-point solvents, biocompatibility, and stability. The lactic acid may be any of L-lactic acid, D-lactic acid, and DL-lactic acid, and the hydrophobic polymer may include one of them alone or two or more of them. Among these lactic acids, from the viewpoint of easily controlling an average particle diameter and from the viewpoint of stability, when the hydrophobic block chain of the amphiphilic block polymer contains an L-lactic acid-derived structural unit, L-lactic acid is preferred, and when the hydrophobic block chain of the amphiphilic block polymer contains a D-lactic acid-derived structural unit, D-lactic acid is preferred.

When the hydrophobic polymer contains a hydroxy acid-derived structural unit, the amount of such a structural unit contained in the hydrophobic polymer is preferably 50 to 100 mol %, more preferably 65 to 100 mol %, further preferably 80 to 100 mo %, particularly preferably 90 to 100 mol %.

It is to be noted that the hydrophobic polymer may contain a structural unit derived from the above-described hydrophobic amino acid.

Although the number-average molecular weight (Mn) of the hydrophobic polymer is not particularly limited, it is preferably 700 to 6,000, more preferably 1,000 to 4,000.

Although the weight-average molecular weight (Mw) of the hydrophobic polymer is not particularly limited, it is preferably 700 to 6,000, more preferably 1,000 to 4,000.

The molecular weight distribution (Mw/Mn) of the hydrophobic polymer is preferably 1.5 or less.

When the hydrophobic polymer is used, the molar ratio between the amphiphilic block copolymer and the hydrophobic polymer contained in the molecular assemblies [(A-1):(A-2)] is preferably 10:1 to 1:10 from the viewpoint of easily controlling the volume of hydrophobic core of the molecular assemblies or the size of the molecular assemblies.

<(B) Drug>

The drug included in the skin external preparation according to the present invention is not particularly limited. The skin external preparation according to the present invention uses the molecular assemblies containing the above-described amphiphilic block copolymer and the drug in combination to reduce skin irritation caused by the drug. Therefore, even when the drug used is highly irritating to the skin, the skin external preparation can be safely administered through the skin.

Specific examples of the drug that can be preferably used include those that have been reported to cause contact dermatitis. These drugs may be used singly or in combination of two or more of them.

Examples of the drugs that have been reported to cause contact dermatitis include statins. Examples of the statins include mevastatin, simvastatin, fluvastatin, lovastatin, atorvastatin, pitavastatin, rosuvastatin, pravastatin, and pharmaceutically-acceptable salts thereof. Examples of the pharmaceutically-acceptable salts include: alkali metal salts such as sodium salts; alkaline-earth metal salts such as calcium salts; ammonium salts; and alkyl ammonium salts. The skin external preparation according to the present invention is easily transferred into blood and the like due to its high skin permeability, which makes it possible to sufficiently exhibit the pharmacological effects of statins.

Among these statins, oil-soluble statins and pharmaceutically-acceptable salts thereof are preferred. Examples of the oil-soluble statins include mevastatin, simvastatin, fluvastatin, lovastatin, atorvastatin, pitavastatin, rosuvastatin, and pharmaceutically-acceptable salts thereof.

Other examples of the drugs that have been reported to cause contact dermatitis include: antibiotics such as fradiomycin sulfate, gentamicin, kanamycin, oxytetracycline hydrochloride, clindamycin phosphate, polymyxin B sulfate, bacitracin, erythromycin, chloramphenicol, sodium fusidate, and silver sulfadiazine; antifungals such as clotrimazole, neticonazole hydrochloride, luliconazole, sulconazole nitrate, bifonazole, lanoconazole, amorolfine hydrochloride, terbinafine hydrochloride, butenafine hydrochloride, and tolnaftate;

non-steroidal anti-inflammatory drugs such as acetylsalicylic acid, bufexamac, ibuprofen, ibuprofen piconol, ufenamate, diclofenac sodium, indomethacin, ketoprofen, loxoprofen, suprofen, tiaprofen, naproxen, flurbiprofen, and piroxicam;

local anesthetics such as procaine hydrochloride, ethyl aminobenzoate, dibucaine hydrochloride, lidocaine hydrochloride, and tolperisone hydrochloride;

antipruritic drugs such as diphenhydramine hydrochloride, crotamiton, L-menthol, glycol salicylate, and methyl salicylate;

steroidal anti-inflammatory drugs such as hydrocortisone acetate, hydrocortisone, predonisolone, triamcinolone acetonide, halcinonide, flucinonide, amcinonide, flucinolone acetonide, dexamethasone, hydrocortisone butyrate, hydrocortisone butyrate propionate, deprodone propionate, prednisolone valerate acetate, clobetasol propionate, clobetasone acetate, betamethasone valerate, dexamethasone valerate, diflucortolone valerate, betamethasone dipropionate, betamethasone butyrate propionate, beclometasone propionate, dexamethasone dipropionate, flumetasone pivalate, alclometasone, mometasone furoate, difluprednate, and diflorasone acetate;

ophthalmic drugs such as phenylephrine hydrochloride, pivalephrine hydrochloride, atropine sulfate, ketotifen fumarate, sodium cromoglycate, amlexanox, tobramycin, dibekacin sulfate, sisomicin sulfate, timolol maleate, nipradilol, befunolol hydrochloride, and levocabastine hydrochloride;

anti-ulcer drugs such as lysozyme chloride and trafermin;

Alzheimer-type dementia treatment drugs such as donepezil hydrochloride, memantine hydrochloride, rivastigmine, rivastigmine tartrate, and galantamine hydrobromide;

antiepileptic drugs such as chloramphenicol, carbamazepine, phenobarbital, phenytoin, etizolam, nitrazepam, idebenone, and mianserin hydrochloride;

antipyretic analgesic drugs such as chloral hydrate, acetylsalicylic acid, tolfenamic acid, and bucolome;

circulatory drugs such as mexiletine hydrochloride, doxazosin mesylate, dipyridamole, and isosorbide nitrate;

respiratory drugs such as dihydrocodeine phosphate and theophyline;

blood-body fluid disease treatment drugs such as ticlopidine hydrochloride, beraprost sodium, and limaprost alfadex; and pollakiuria treatment drugs such as oxybutynin hydrochloride.

Among these other drugs that have been reported to cause contact dermatitis, Alzheimer-type dementia treatment drugs and pollakiuria treatment drugs are preferred.

<Forms of Skin External Preparation>

The skin external preparation according to the present invention includes: the nanometer-size molecular assemblies containing the above-described amphiphilic block copolymer; and the above-described drug. The dosage form of the skin external preparation according to the present invention is not particularly limited, and examples thereof include external liquids, lotions, tonics, liniments, emulsions, gels, ointments, creams, pastes, plasters, compresses, poultices, plasters, tapes, reserver-type patches, sprays, aerosols, foams, skin lotions, and packs.

The skin external preparation includes the drug and the molecular assemblies, which means that the drug and the molecular assemblies are present in the skin external preparation. The drug may be contained in polymer nano-particles as the molecular assemblies containing the above-described amphiphilic block copolymer and the above-described optional hydrophobic polymer. It is to be noted that the term "contain" includes the concepts of "encapsulate" and "carry". When the molecular assemblies contain the drug, the molecular assemblies themselves have both functions as a drug and a skin irritation-reducing agent.

Examples of the form of the skin external preparation including the drug and the molecular assemblies encompasses, in addition to a form in which the molecular assemblies contain the drug, a form in which the molecular assemblies and the drug are present (coexist) in a mixed state and a form in which a region containing the molecular assemblies and a region containing the drug are present. In these forms, the molecular assemblies function as a skin irritation-reducing agent.

The skin external preparation having a molecular assembly-containing region and a drug-containing region is in the form of, for example, a skin patch including a base material, a drug-containing layer on the base material, and a molecular assembly-containing layer provided on the skin-contact side of the drug-containing layer. Such a skin patch for external use includes, on a base material, a drug-containing layer as the drug-containing region and a molecular assembly-containing layer as the molecular assembly-containing region for reducing skin irritation in this order.

When the molecular assemblies are used as a skin irritation-reducing agent, the effect of reducing skin irritation can be obtained by bringing the molecular assemblies into contact with the epidermis by application or the like and then applying the drug onto the molecular assemblies.

The amount of the drug contained in the skin external preparation is, for example, about 0.0001 to 50 mass % with respect to the total amount of the skin external preparation. From the viewpoint of skin irritation reduction, skin permeability, and pharmacological effects, the amount of the drug contained in the skin external preparation is preferably 0.001 to 30 mass %, more preferably 0.01 to 15 mass %, further preferably 0.05 to 10 mass %, further preferably 0.1 to 5 mass % with respect to the total amount of the skin external preparation. Particularly, from the viewpoint of skin permeability and pharmacological effects, the amount of the drug contained in the skin external preparation is further preferably 0.15 to 2.5 mass %, further preferably 0.2 to 1.5 mass %, particularly preferably 0.3 to 1 mass %.

The amount of the amphiphilic block copolymer contained in the skin external preparation is, for example, about 0.0001 to 50 mass %, preferably 0.001 to 30 mass %, more preferably 0.01 to 20 mass %, particularly preferably 0.1 to 10 mass % with respect to the total amount of the skin external preparation.

The molar ratio between the amphiphilic block copolymer and the drug contained in the skin external preparation [(A-1):(B)] is preferably 1:1000 to 1000:1, more preferably 1:100 to 100:1, further preferably 1:100 to 1:1, particularly preferably 1:50 to 1:1.

<Molecular Assemblies>

The molecular assemblies used in the present invention are each a structure formed by aggregation or self-assembling orientation and association of the above-described amphiphilic block copolymer. The molecular assemblies may have any of shapes including a particulate shape (e.g., a micelle or vesicle shape), a rod shape, and another form of molecular aggregate. From the viewpoint of skin irritation reduction, skin permeability, and pharmacological effects, the molecular assemblies preferably have a particulate shape, more preferably a micelle shape or a vesicle shape, particularly preferably a micelle shape.

From the viewpoint of skin irritation reduction, skin permeability, and pharmacological effects, the average particle diameter of the molecular assemblies used in the present invention is preferably 10 to 300 nm, more preferably 10 to 200 nm, further preferably 10 to 150 nm, further preferably 10 to 100 nm, further preferably 15 to 60 nm, particularly preferably 20 to 45 nm.

It is to be noted that the average particle diameter refers to a value measured by a method that will be described later in Examples.

The skin external preparation and the skin irritation-reducing agent according to the present invention can be produced by adding molecular assemblies obtained in the following manner in accordance with an ordinary method.

Molecular assemblies can be formed by a film method, an injection method, or the like using the amphiphilic block copolymer, which can be synthesized by a known method in which a peptide synthesis method, a polyester synthesis method, and a depsipeptide synthesis method are appropriately combined, and, as necessary, the hydrophobic polymer. Drug-containing molecular assemblies can be obtained by using, in the process of forming molecular assemblies, the drug in addition to the amphiphilic block copolymer and the optional hydrophobic polymer. Further, the amphiphilic block copolymer before formed into molecular assemblies and the optional hydrophobic polymer may be provided as skin irritation-reducing agents. In this embodiment, molecular assemblies usable as a skin external preparation can be obtained by forming molecular assemblies using the amphiphilic block copolymer as a skin irritation-reducing agent and the drug. The obtained molecular assemblies may be subjected to surface modification by a known method.

(Film Method)

A film method is a method generally used for preparing liposomes, and includes the following steps (1) to (3);

dissolving the amphiphilic block copolymer, the drug, and, if necessary, the hydrophobic polymer in an organic solvent in a container (e.g., a glass container) to obtain a solution (step (1));

removing the organic solvent from the solution to obtain, on an inner wall of the container, a film containing the amphiphilic block copolymer and, if necessary, the hydrophobic polymer and/or the drug (step (2)); and adding water or an aqueous solution to the container to convert the film into particulate molecular assemblies to obtain a molecular assembly dispersion liquid (step (3)).

The film method may further include the step of subjecting the molecular assembly dispersion liquid to freeze-drying treatment. In the step (3), ultrasonic treatment and heating treatment of the aqueous solution may be performed, if necessary.

The solution in which the amphiphilic block copolymer and, if necessary, the hydrophobic polymer and/or the drug are contained in the organic solvent is appropriately prepared by those skilled in the art. For example, the solution may be prepared by mixing all the polymer and the drug that should be used at one time, or may be prepared by previously preparing part of the polymer and the drug that should be used in the form of film and then adding a solution containing the remaining components that should be used. The previously-prepared film of part of the polymer can be formed in accordance with a method that will be described later.

The organic solvent used in the film method is not particularly limited as long as the amphiphilic block copolymer, the drug, and the hydrophobic polymer can be dissolved therein. A low-boiling-point solvent is preferably used because the organic solvent is distilled off after dissolution. In the present invention, the low-boiling-point solvent refers to one having a boiling point of 100° C. or less, preferably 90° C. or less at one atmospheric pressure.

Specific examples of the low-boiling-point solvent include chloroform, diethyl ether, acetonitrile, methanol, ethanol, propanol, isopropanol, acetone, dichloromethane, tetrahydrofuran, hexane, and ethyl acetate.

When such a low-boiling-point solvent is used to dissolve the amphiphilic block copolymer and, if necessary, the hydrophobic polymer and/or the drug, it is very easy to remove the solvent. A method for removing the solvent is not particularly limited, and may be appropriately determined by those skilled in the art depending on the boiling point of the organic solvent used. For example, the solvent may be removed under reduced pressure or by natural drying.

After the organic solvent is removed, a film containing the amphiphilic block copolymer and, if necessary, the hydrophobic polymer and/or the drug is formed on an inner wall of the container. Water or an aqueous solution is added to the container having the film attached to the inner wall thereof. The water or the aqueous solution is not particularly limited, and may be appropriately selected by those skilled in the art from biochemically or pharmaceutically acceptable ones such as distilled water for injection, normal saline, and buffer solutions.

After adding the water or the aqueous solution, warming treatment and/or ultrasonic treatment may be performed, as necessary. As a result, molecular assemblies are formed in the process of peeling-off of the film from the inner wall of the container. The ultrasonic treatment may be performed under conditions of, for example, 1 to 60 minutes. The warming treatment may be performed under conditions of, for example, 20 to 95° C. When the ultrasonic treatment and the warming treatment are performed at the same time, the ultrasonic treatment may be performed under conditions of, for example, 20 to 95° C. and 1 to 60 minutes. After the completion of the warming treatment and/or the ultrasonic treatment, a dispersion liquid is prepared in the container, in which the molecular assemblies are dispersed in the water or the aqueous solution.

(Injection Method)

An injection method is a method used to prepare not only the molecular assemblies according to the present invention but also many other molecular assemblies. According to this method, molecular assemblies can be prepared by dissolving the amphiphilic block copolymer and, as necessary, the hydrophobic polymer and/or the drug in an organic solvent such as trifluoroethanol, ethanol, hexafluoroisopropanol, or dimethyl sulfoxide to obtain a solution; dispersing the solution in a water-based solvent such as distilled water for injection, normal saline, or a buffer solution; performing purification treatment such as gel filtration chromatography, filtering, or ultracentrifugation; and then removing the organic solvent.

When the molecular assemblies are prepared as encapsulation-type vesicles, a solution obtained by dissolving the amphiphilic block copolymer and, as necessary, the hydrophobic polymer and/or the drug in the above-described organic solvent may be dispersed in an aqueous solution or a suspension liquid obtained by dissolving or suspending, in a water-based solvent such as distilled water for injection, normal saline, or a buffer solution, a substance that should be encapsulated.

When drug-containing molecular assemblies are formed by using the drug in the process of forming molecular assemblies, a hydrophobic drug is preferably used from the viewpoint of easily encapsulating or carrying the drug to reduce skin irritation. For example, when fat-soluble statin is used as the drug, the drug is easily encapsulated in or carried by the hydrophobic core of the amphiphilic block copolymer so that skin irritation is further reduced.

From the viewpoint of appearance stability such as coarsening of particles or aggregation of the leaked drug, the molar ratio between the amphiphilic block copolymer and the drug contained in the skin external preparation [(A-1):(B)] is preferably 1:1000 to 1000:1, more preferably 1:100 to 100:1, further preferably 1:100 to 1:1, particularly preferably 1:50 to 1:1.

<Additional Component of Skin External Preparation>

In addition to the above-described molecular assemblies and drug, the skin external preparation according to the present invention may include a moisturizer, a softener, a transdermal absorption promoter, a soothing agent, a preservative, an antioxidant, a colorant, a thickener, a perfume, a pH controller, and the like. They may be used singly or in combination of two or more of them.

Examples of the moisturizer include agar, diglycerol, distearyldimonium hectorite, butylene glycol, polyethylene glycol, propylene glycol, hexylene glycol, coix seed extract, Vaseline, urea, hyaluronic acid, tranexamic acid, ceramide, Lipidure, isoflavone, amino acid, collagen, mucopolysaccharide, fucoidan, lactoferrin, sorbitol, chitin-chitosan, malic acid, glucuronic acid, placenta extract, seaweed extract, moutan cortex extract, *Hydrangea serrata* leaf extract, *Hypericum perforatum* extract, Coleus extract, *Euonymus japonicus* extract, safflower extract, Rugosa rose extract, *Polyporus umbellatus* extract, *Crataegus cuneata* extract, rosemary extract, *Lansium domesticum* extract, chamomile extract, *Lamium album* extract, *Ganoderma lucidum* stem extract, *Achillea millefolium* extract, aloe extract, *Aesculus hippocastanum* extract, *Thujopsis dolabrata* extract, *Fucus vesiculosus* extract, Osmoin extract, oat bran extract, tuberosa polysaccharide, plant worm extract, barley extract, orange extract, Rehmannia root extract, Japanese pepper extract, and coix seed extract.

Examples of the softener include glycerol, mineral oil, and emollient components (e.g., isopropyl isostearate, polyglyceryl isostearate, isotridecyl isononanoate, octyl isononanoate, oleic acid, glyceryl oleate, cacao oil, cholesterol, mixed fatty acid triglyceride, dioctyl succinate, sucrose tetrastearate triacetate, cyclopentasiloxane, sucrose distearate, octyl palmitate, octyl hydroxystearate, arachidyl behenate, sucrose polybehenate, polymethylsilsesquioxane, myristyl alcohol, cetyl myristate, myristyl myristate, and hexyl laurate).

Examples of the transdermal absorption promoter include ethanol, isopropyl myristate, citric acid, squalene, oleic acid, menthol, N-methyl-2-pyrrolidone, diethyl adipate, diisopropyl adipate, diethyl sebacate, diisopropyl sebacate, isopropyl palmitate, isopropyl oleate, octyldodecyl oleate, isostearyl alcohol, 2-octyl dodecanol, urea, vegetable oils, and animal oils.

Examples of the soothing agent include benzyl alcohol, procaine hydrochloride, xylocaine hydrochloride, and chlorobutanol.

Examples of the antiseptic include benzoic acid, sodium benzoate, paraben, ethylparaben, methylparaben, propylparaben, butylparaben, potassium sorbate, sodium sorbate, sorbic acid, sodium dehydroacetate, hydrogen peroxide, formic acid, ethyl formate, sodium hypochlorite, propionic acid, sodium propionate, calcium propionate, pectin digests, polylysine, phenol, isopropyl methyl phenol, o-phenyl phenol, phenoxy ethanol, resorcin, thymol, thiram, and tea tree oil.

Examples of the antioxidant include vitamin A, retinoic acid, retinol, retinol acetate, retinol palmitate, retinyl acetate, retinyl palmitate, tocopheryl retinoate, vitamin C and derivatives thereof, kinetin, β-carotene, astaxanthin, lutein, lycopene, tretinoin, vitamin E, α-lipoic acid, coenzyme Q10, polyphenol, SOD, and phytic acid.

Examples of the colorant include iron oxide, diiron trioxide, yellow ferric oxide, titanium dioxide, kaoline, tar-based dyes, and chlorophyll.

Examples of the thickener include quince seed, carrageenan, gum arabic, karaya gum, xanthan gum, gellan gum, tamarind gum, locust beam gum, tragacanth gum, pectin, starch, cyclodextrin, methyl cellulose, ethyl cellulose, carboxymethyl cellulose, sodium alginate, polyvinyl alcohol, polyvinyl pyrrolidone, carboxy vinyl polymer, and sodium polyacrylate.

Examples of the perfume include musk, acacia oil, anise oil, ilang-ilang oil, cinnamon oil, jasmine oil, sweet orange oil, spearmint oil, geranium oil, thyme oil, neroli oil, mint oil, cypress oil, fennel oil, peppermint oil, bergamot oil, lime oil, lavender oil, lemon oil, lemongrass oil, rose oil, rosewood oil, anisaldehyde, geraniol, citral, civetone, muscone, limonene, and vanillin.

Examples of the pH controller include citric acid, sodium citrate, acetic acid, sodium acetate, sodium hydroxide, potassium hydroxide, phosphoric acid, sodium hydrogen phosphate, sodium dihydrogen phosphate, disodium hydrogen phosphate, succinic acid, sodium succinate, malic acid, sodium malate, and hydrochloric acid.

<Administration of Skin External Preparation>

The skin external preparation according to the present invention is intended for transdermal administration (including transmucosal administration). The skin external preparation according to the present invention can be expected to have not only local action but also systemic action, and is therefore useful as a skin external preparation for use in preventing or treating systemic diseases such as circulatory diseases, immunological diseases, mental diseases, nervous system diseases, and endocrine diseases.

The dose and the duration of dosing of the skin external preparation according to the present invention can be appropriately set depending on the type and amount of drug used, the body weight of a patient, and disease status.

The skin external preparation according to the present invention has reduced skin irritation by the drug and a high level of safety for humans, is easily transferred into the body (e.g., into the blood) through the skin, and has excellent pharmacological effects. Further, the skin external preparation according to the present invention is excellent in biodegradability and biocompatibility, and can further be expected to develop its drug efficacy in the body even in a small amount.

Particularly, the skin external preparation according to the present invention can develop excellent pharmacological effects even when using a drug that is difficult to develop desired drug efficacy simply by applying it onto the skin, or can achieve both development of excellent pharmacological effects and reduction in the risk of side effects even when using a drug unsuitable for external application due to its high risk of side effects such as skin irritation.

EXAMPLES

Hereinbelow, the present invention will be described in detail with reference to examples, but is not limited to these examples.

In the examples, an average particle diameter was measured with Zetasizer Nano S (manufactured by Malvern Instruments) using a sample prepared by dispersing molecular assemblies contained in an evaluation solution in purified water at a concentration of 1 mg/mL. Measurement parameters were 1.330 (Dispersant RI) and 1.45 (Material RI) (protein), and a measurement temperature was 25.0° C. Data analysis was performed using Zetasizer Software (ver. 6.32).

Synthesis Example 1: Synthesis of Polysarcosine-Poly-L-Lactic Acid (Psar-PLLA)

According to the following procedure, a polysarcosine-polylactic acid amphiphilic block polymer ($PSar_{65}$-$PLLA_{30}$) was synthesized from sarcosine-NCA (Sar-NCA) and aminated poly-L-lactic acid (a-PLA) (Scheme 1).

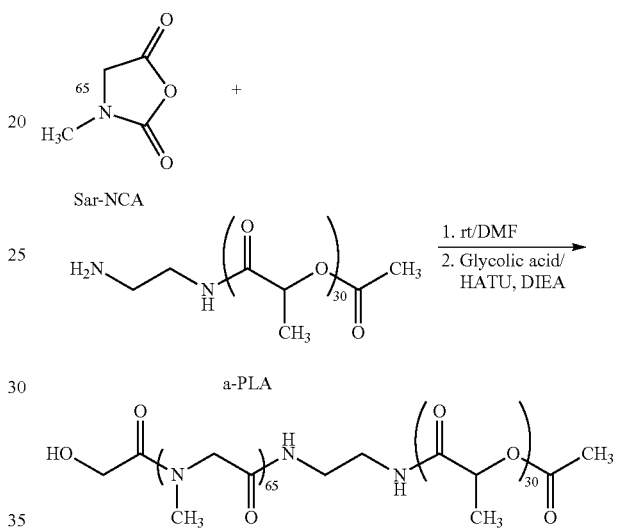

Dimethyl formamide (DMF) (140 mL) was added to aminated poly-L-lactic acid (383 mg, 0.17 mmol) and sarcosine-NCA (3.21 g, 27.9 mmol) in an argon atmosphere, and the resulting mixture was stirred at room temperature for 12 hours. Then, the reaction solution was cooled to 0° C. and mixed with glycolic acid (72 mg, 0.95 mmol), o-(benzotriazole-1-yl)-N,N,N',N'-tetramethyluronium hexafluorophosphate (HATU) (357 mg, 0.94 mmol), and N,N-diisopropylethylamine (DIEA) (245 μL, 1.4 mmol) to perform a reaction at room temperature for 18 hours.

Then, DMF was distilled off with a rotary evaporator under reduced pressure, and purification was performed using an LH20 column. Fractions with a peak detected at UV 270 nm were collected and concentrated. The obtained concentrated solution was dropped into diethyl ether at 0° C. to cause reprecipitation to obtain $PSar_{65}$-$PLLA_{30}$ (1.7 g) as a desired product.

Example 1: Effect of Reducing Skin Irritation Caused by Pitavastatin Calcium

In Example 1, amphiphilic polymer micelles containing pitavastatin calcium as a drug were prepared as a skin external preparation, and tests were performed using the skin external preparation.

Preparation Example 1-1: Preparation of Pitavastatin Calcium-Containing Polymer Micelles (35 nm)

100 mg of $PSar_{65}$-$PLLA_{30}$ obtained in Synthesis Example 1, and 20 mg of pitavastatin calcium were dissolved in 40 mL of chloroform, and then the chloroform was distilled off with a rotary evaporator under reduced pressure. After the distillation off under reduced pressure, 10 mL of purified water was added to a thin film formed in a container. Then, the container was immersed in a hot bath at 85° C. for 20 minutes to form micelles, and a filtrate was obtained by filtration using a 0.2 μm PTFE filter and freeze-dried to obtain pitavastatin calcium-containing polymer micelles.

The polymer micelles had an average particle diameter of 35 nm and a drug content of 20 mass %, and the collection rate of the polymer micelles was 90% or more.

Preparation Example 1-2: Preparation of Pitavastatin Calcium-Containing Polymer Micelles (60 nm)

First, 100 mg of $PSar_{65}$-$PLLA_{30}$ obtained in Synthesis Example 1, 34 mg of poly-L-lactic acid ($PLLA_{30}$-Z) whose terminal was protected with a Z (benzyloxycarbonyl) group, and 20 mg of pitavastatin calcium were dissolved in 10 mL of chloroform, and then the chloroform was distilled off with a rotary evaporator under reduced pressure. After the distillation off under reduced pressure, 10 mL of purified water was added to a thin film formed in a container. Then, the container was immersed in a hot bath at 85° C. for 20 minutes to form micelles, and a filtrate was obtained by filtration using a 0.2 μm PTFE filter and freeze-dried to obtain pitavastatin calcium-containing polymer micelles.

The polymer micelles had an average particle diameter of 60 nm and a drug content of 15 mass %, and the collection rate of the polymer micelles was 90% or more.

Preparation Example 1-3: Preparation of Pitavastatin Calcium-Containing Polymer Micelles (35 nm)

Pitavastatin calcium-containing polymer micelles were obtained in the same manner as in Preparation Example 1-1 except that the amount of pitavastatin calcium was changed to 10 mg.

The polymer micelles had an average particle diameter of 35 nm and a drug content of 10 mass %, and the collection rate of the polymer micelles was 90% or more.

Preparation Example 1-4: Preparation of Pitavastatin Calcium-Containing Polymer Micelles (35 nm)

Pitavastatin calcium-containing polymer micelles were obtained in the same manner as in Preparation Example 1-1 except that the amount of pitavastatin calcium was changed to 40 mg.

The polymer micelles had an average particle diameter of 35 nm and a drug content of 40 mass %, and the collection rate of the polymer micelles was 90% or more.

Test Example 1-1: Skin Irritation Test

In consideration of skin conditions, test animals (rabbits) were selected. On the day before the start of administration, hair on the back of each test animal was shaved with electric clippers and a shaver. A 2.5-cm square cut piece of lint fabric was impregnated with 500 μL of each of the following liquids <1-A> to <1-E> as a test sample, protected with oiled paper (hereinafter, referred to as a preparation), and attached to the skin of the back. The preparation was administered by closed application. After being applied, the preparation was covered with a medical adhesive sheet to prevent the slippage of the lint fabric, and was further fixed with surgical tape. An Elizabethan collar was placed on each of the animals.

After 24 hours from the application, the Elizabethan collar was removed, and the preparation was removed (wiped out) with absorbent cotton soaked with normal saline (Japanese Pharmacopoeia isotonic sodium chloride solution, OTSUKA NORMAL SALINE, manufactured by Otsuka Pharmaceutical Factory, Inc.), and the administration site was observed. Then, the next application of the preparation was performed. In this way, the administration and the observation were repeated for continuous 14 days.

The observation was performed with the naked eye to observe erythema, eschar, and edema. The degree of skin irritation was evaluated based on the total of the score of erythema and eschar and the score of edema in accordance with criteria for skin irritation of Draize method. The scores for evaluation of erythema and eschar and the scores for evaluation of edema are shown in Table 1, and test results obtained by statistical analysis based on Dunnett method are shown in FIG. 1.

<1-A>: Phosphate buffer (pH 7.4) suspension liquid prepared in such a manner that the concentration of the pitavastatin calcium-containing polymer micelles obtained in Preparation Example 1-1 was 0.5 mass % in terms of pitavastatin calcium <1-B>: Phosphate buffer (pH 7.4) suspension liquid including pitavastatin calcium (0.5 mass %) and macrogol 400 (9 mass %)

<1-C>: Phosphate buffer (pH 7.4) suspension liquid including pitavastatin calcium (0.5 mass %)

<1-D>: Phosphate buffer (pH 7.4) suspension liquid including the polymer obtained in Synthesis Example 1 (2.5 mass %)

<1-E>: Phosphate buffer (pH 7.4)

TABLE 1

| | | Scores for evaluation |
|---|---|---|
| Erythema and Eschar | No erythema | 0 |
| | Very slight erythema (barely perceptible) | 1 |
| | Clear erythema | 2 |
| | Moderate to severe erythema | 3 |
| | Severe erythema (beet redness) to slight eschar formation (injuries in depth) | 4 |
| Edema | No edema | 0 |
| | Very slight edema (barely perceptible) | 1 |
| | Slight edema (edges of area well defined by definite raising) | 2 |
| | Moderate edema (raised approximately about 1 mm) | 3 |
| | Severe edema (raised 1 mm or more and extending beyond the area of exposure) | 4 |

As a result of Test Example 1-1, it was confirmed that when the pitavastatin calcium-containing polymer micelle suspension liquid (liquid 1-A) was used, the skin irritation score was significantly reduced as compared to when the pitavastatin calcium suspension liquid (liquid 1-C) was used. Further, the skin irritation score of the pitavastatin calcium-containing polymer micelle suspension liquid (liquid 1-A) hovered at 1 or less for 14 days, and unexpectedly hovered at almost the same level as the polymer micelle suspension liquid containing no pitavastatin (liquid 1-D).

Further, the result of skin irritation evaluation of the solution prepared by dissolving pitavastatin calcium in macrogol 400 solution (liquid 1-B) did not show a tendency of extreme increase in cumulative irritation score, but the skin irritation score of the solution (liquid 1-B) was higher than that of the pitavastatin calcium-containing polymer micelle suspension liquid (liquid 1-A).

Test Example 1-2: Skin Permeation Test (1)

Figure 2:
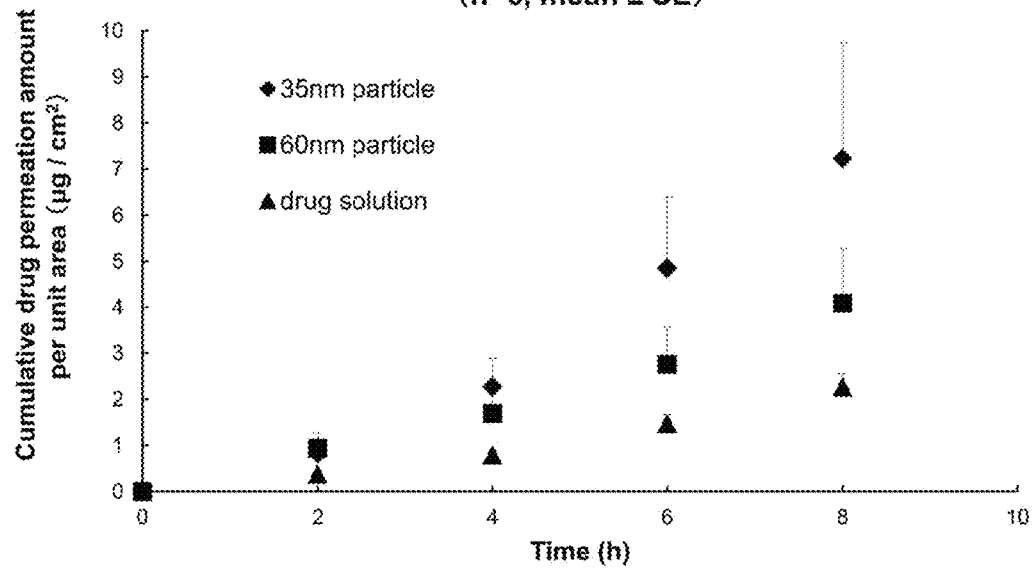
FIG. 2 is a graph showing the results of a skin permeation test for pitavastatin.

The abdominal skin of a rat was subjected to hair removal treatment and then excised to be used as a permeation membrane. The excised skin was fixed to a horizontal diffusion cell in such a manner that the stratum corneum of the excised skin faced the donor side. The pitavastatin calcium-containing polymer micelles obtained in Preparation Examples 1-1 and 1-2 and pitavastatin calcium as a control were each suspended in a phosphate buffer solution (pH 7.4) so that the concentration of pitavastatin calcium was 0.1 mass %, and the resulting donor solutions were applied to the fixed excised rat skin. A receptor solution was 2 mL of a phosphate buffer solution (pH 7.4). After the start of experiment, 0.5 mL of the receptor solution was collected from a sampling port with time and 0.5 mL of a fresh receptor solution was supplied. The amount of pitavastatin contained in the collected sample solution was measured by HPLC to determine the amount of permeated pitavastatin calcium of each of the preparations through the rat skin. The test results are shown in FIG. 2.

Test Example 1-3: Skin Permeation Test (2)

Figure 3:
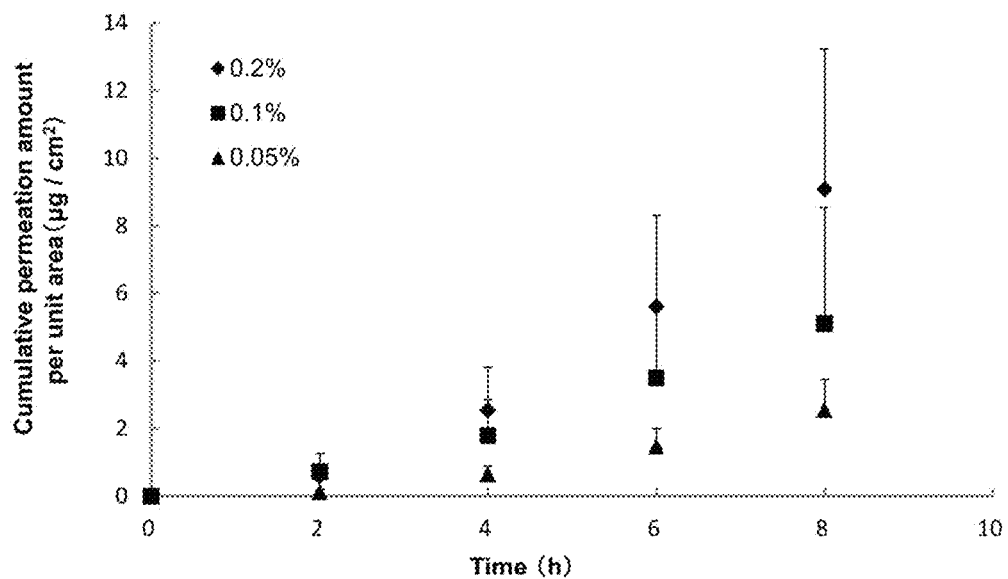
FIG. 3 is a graph showing the results of a skin permeation test for pitavastatin.

The pitavastatin calcium-containing polymer micelles obtained in Preparation Examples 1-1, 1-3, and 1-4 were each suspended in a phosphate buffer solution (pH 7.4) so that the concentrations of pitavastatin calcium were 0.1 mass %, 0.05 mass %, and 0.2 mass % to prepare samples, and skin permeability was measured using the samples in the same manner as in Test Example 1-2. The results are shown in FIG. 3.

From the results of Test Examples 1-2 and 1-3, it was confirmed that the pitavastatin calcium-containing polymer micelles had high skin permeability.

Test Example 1-4: Drug Efficacy Test

On the day before the start of administration, hair on the back of each test animal (male guinea pig, Slc: Hartley, 7-week old) was shaved with electric clippers and a shaver and removed with a depilatory cream (epilat manufactured by Kanebo). The hair removal site of each test animal was covered with sponge packing with tape (3.5 cm×3.5 cm×0.5 cm, manufactured by Ashiya Packing Co., Ltd.) to prevent dripping, and 500 µL of each of the following liquids <4-A> to <4-E> was applied to a 2.5 cm×2.5 cm site provided by cutting out the inside of the sponge packing. The administered liquid was spread on the application site, and was then absorbed by a 2.5 cm-square cut piece of lint fabric (hereinafter, referred to as a preparation). The preparation was administered by closed application. Three silicone sheets were laminated on the lint fabric soaked with the administered liquid, and the preparation was fixed with medical surgical tape and a stretch bandage. After 24 hours from the application, the preparation was removed (wiped out) with absorbent cotton soaked with normal saline (Japanese Pharmacopoeia isotonic sodium chloride solution, OTSUKA NORMAL SALINE, manufactured by Otsuka Pharmaceutical Factory, Inc.). The administration site was observed, and then the next application of the preparation was performed. In this way, the preparation was continuously applied for 10 days. On day 5 after the start of administration, hair in a site other than the application site was removed with a depilatory cream to maintain the adhesive strength of the sponge form.

Figures 1, 4:
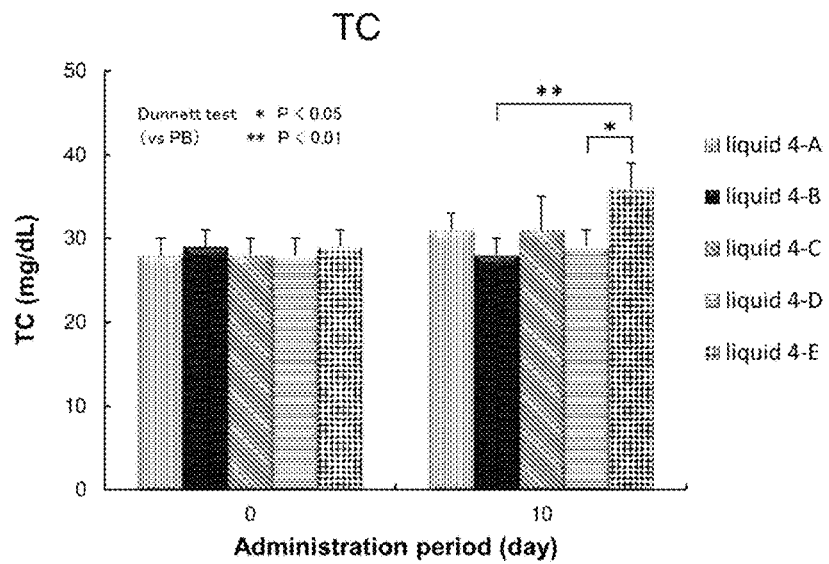
Figures 2, 4:
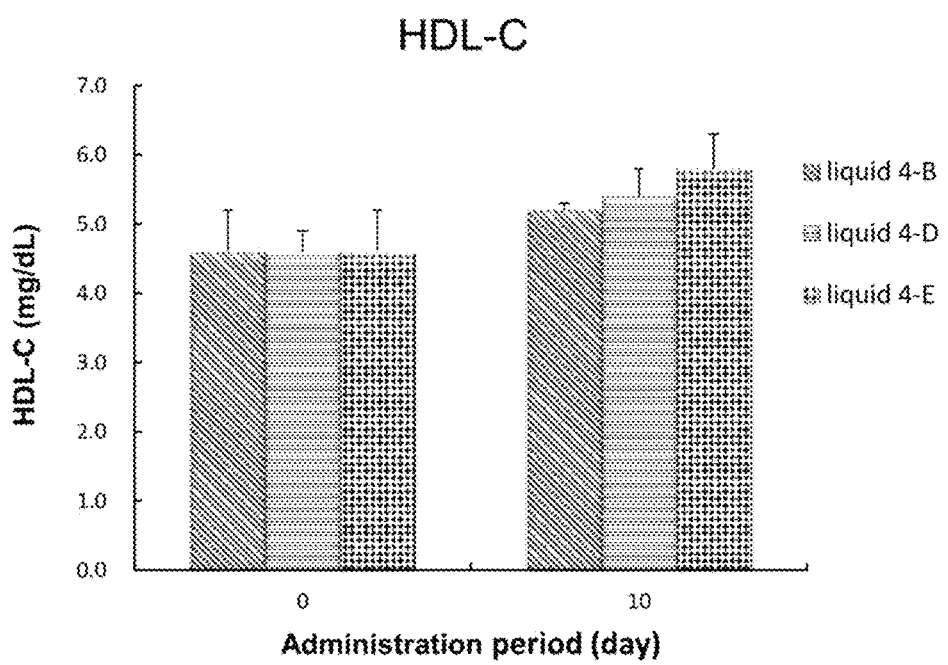
Figures 3, 4:
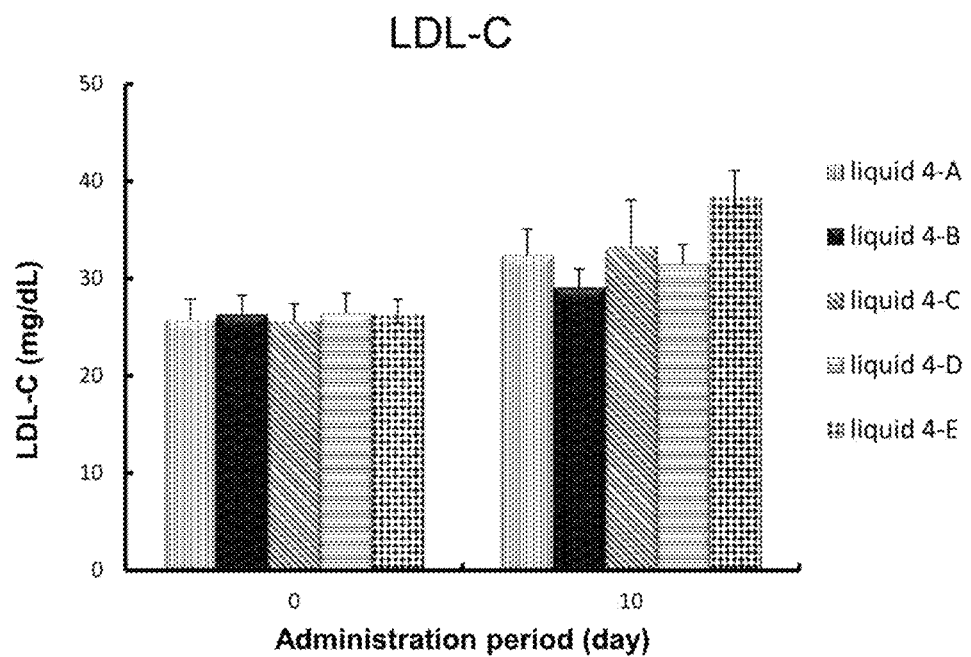
Figure 4:
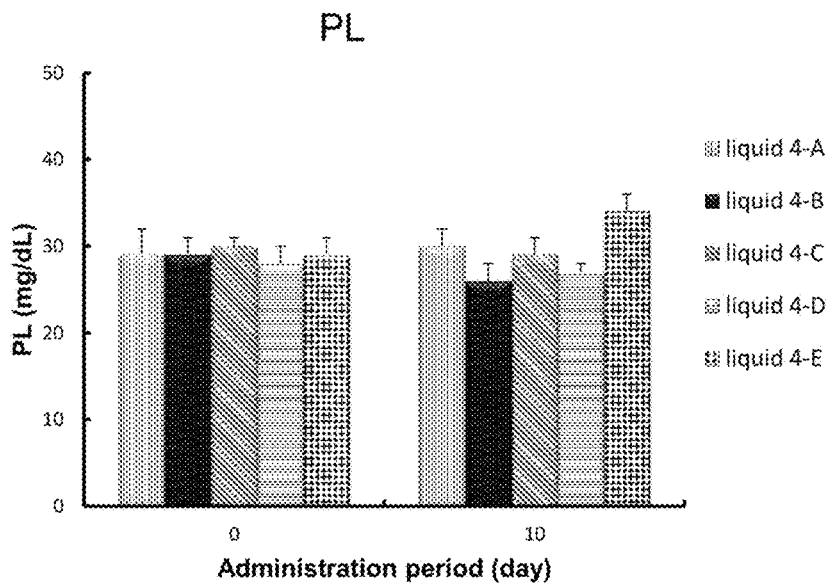

On day 0 and day 10 after the start of administration, about 2.5 mL of blood was collected and centrifuged at 4° C. and 3300 rpm for 15 minutes to obtain blood plasma. The obtained blood plasma was analyzed with an autoanalyzer (LABOSPECT 003) manufactured by Hitachi to measure the amount of total cholesterol (TC), the amount of HDL cholesterol (HDL-C), the amount of LDL cholesterol (LDL-C), and the amount of phospholipid (PL). The results are shown in FIGS. 4-1 to 4-4.

<4-A>: Phosphate buffer (pH 7.4) suspension liquid prepared in such a manner that the concentration of the pitavastatin calcium-containing polymer micelles obtained in Preparation Example 1-1 was 0.1 mass % in terms of pitavastatin calcium <4-B>: Phosphate buffer (pH 7.4) suspension liquid prepared in such a manner that the concentration of the pitavastatin calcium-containing polymer micelles obtained in Preparation Example 1-1 was 0.5 mass % in terms of pitavastatin calcium <4-C>: Phosphate buffer (pH 7.4) suspension liquid including pitavastatin calcium (0.1 mass %)

<4-D>: Phosphate buffer (pH 7.4) suspension liquid including pitavastatin calcium (0.5 mass %)

<4-E>: Phosphate buffer (pH 7.4)

As can be seen from the test results shown in FIGS. 4-1 to 4-4, the pitavastatin calcium-containing polymer micelle suspension liquids (liquid 4-A and liquid 4-B) reduce all the amount of total cholesterol, the amount of HDL cholesterol, the amount of LDL cholesterol, and the amount of phospholipid.

As shown in FIGS. 4-1 and 4-3, when the pitavastatin calcium (0.1 mass %)-containing polymer micelle suspension liquid (liquid 4-A) was used, the amount of total cholesterol and the amount of LDL cholesterol were reduced to the same levels as when the phosphate buffer solution containing 0.1 mass % of pitavastatin calcium (liquid 4-C) was used. Further, as shown in FIGS. 4-1, 4-3 and 4-4, when the pitavastatin calcium (0.5 mass %)-containing polymer micelle suspension liquid (liquid 4-B) was used, the amount of total cholesterol, the amount of LDL cholesterol, and the amount of phospholipid were reduced as compared to when the phosphate buffer solution containing 0.5 mass % of pitavastatin calcium (liquid 4-D) was used.

Test Example 1-5: Irritation Test Using Three-Dimensional Skin Model

The following <5-A> to <5-G> were used as test materials to perform exposure of the epidermis to the test materials and irritation evaluation in the following manner in accordance with OECD TG439 (In Vitro skin irritation test) using a kit for skin irritation test approved by OECD (EPI-212SIT manufactured by KURABO).

Figure 5:
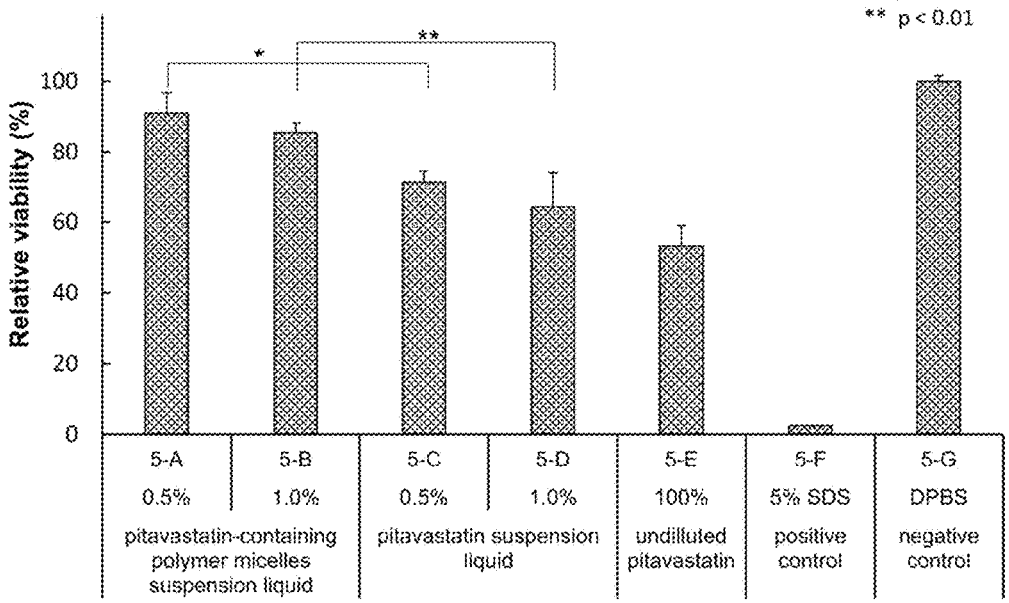
FIG. 5 is a graph showing the results of an irritation test for pitavastatin with the use of a three-dimensional skin model.

The epidermis in the kit was pre-incubated overnight, and then 30 µL of the test material was added to the stratum corneum side of the epidermis, and a nylon mesh was placed with tweezers to expose the stratum corneum to the test material. When the test material was solid (<5-E> described below), 25 µL of DPBS was added to the stratum corneum, and immediately after that, 25 mg of the solid material was added to the stratum corneum to expose the stratum corneum to the test material. After 60 minutes, the test material was completely removed by washing. Then, post-incubation was performed for 42 hours. In the process of the post-incubation, a culture medium was replaced once after a lapse of 24 hours. After the post-incubation, a reaction with an MTT solution was performed for 3 hours using an MTT assay kit (MTT-100-JP manufactured by KURABO), and a formazan dye produced by mitochondrial metabolism was extracted to measure the OD value. Based on the measurement result, relative viability was calculated by comparison with a negative control (<5-G> described below). The test results are shown in FIG. 5.

<5-A>: Phosphate buffer (pH 7.4) suspension liquid prepared in such a manner that the concentration of the pitavastatin calcium-containing polymer micelles obtained in Preparation Example 1-1 was 0.5 mass % in terms of pitavastatin calcium <5-B>: Phosphate buffer (pH 7.4) suspension liquid prepared in such a manner that the concentration of the pitavastatin calcium-containing polymer micelles obtained in Preparation Example 1-1 was 1.0 mass % in terms of pitavastatin calcium <5-C>: Phosphate buffer (pH 7.4) suspension liquid including pitavastatin calcium (0.5 mass %)

<5-D>: Phosphate buffer (pH 7.4) suspension liquid including pitavastatin calcium (1.0 mass %)

<5-E>: Undiluted pitavastatin calcium (powder)

<5-F>: 5% SDS solution; positive control

<5-G>: Dulbecco's Phosphate Buffered Saline (DPBS); negative control

From the test results shown in FIG. 5, it was confirmed that in the test using a three-dimensional skin model, the relative viability was reduced in a manner dependent on the concentration of pitavastatin calcium applied, and was increased by applying the pitavastatin calcium-containing polymer micelles. These results were similar to the results of the cumulative irritation evaluation test using rabbits (Test Example 1-1 described above), that is, the irritation evaluation test using a three-dimensional skin model replicated the results of the animal testing, which suggested that allowing the polymer micelles to contain the drug was effective at reducing skin irritation in a cell system.

Test Example 1-6: Skin Permeation Test Using Three-Dimensional Skin Model

Figure 6:
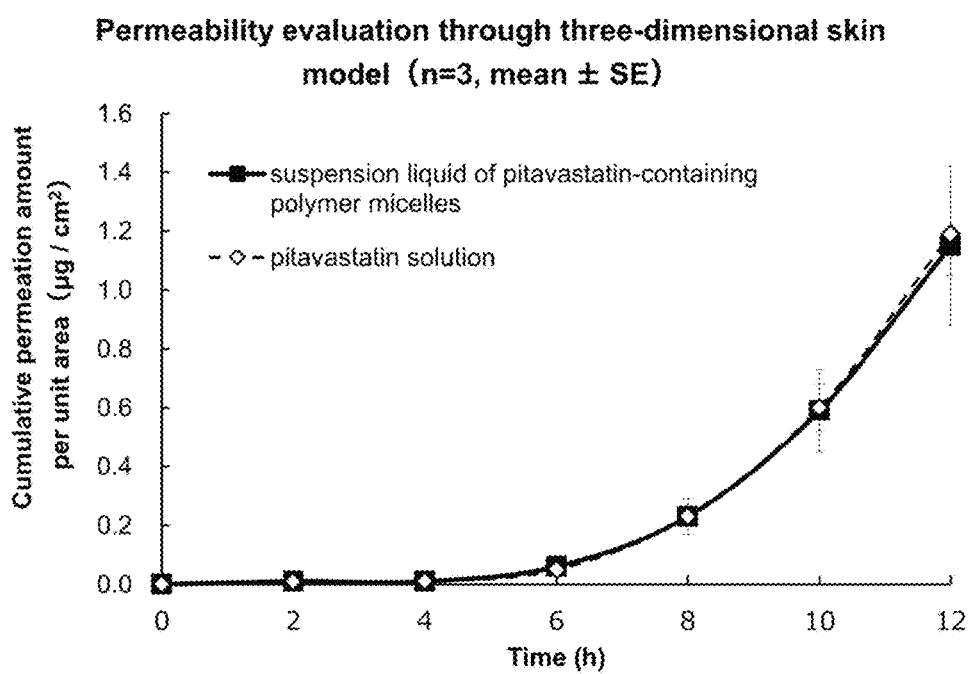
FIG. 6 is a graph showing the results of a permeation test for pitavastatin with the use of a three-dimensional skin model.

A cultured skin model (EPI-606X manufactured by KURABO; enhanced barrier function, recommended product for absorption test) was fixed to a vertical diffusion cell of a transdermal absorption tester with automatic sampling function (TransView manufactured by CosMED Pharmaceutical Co., Ltd.) so that the stratum corneum of the skin model faced the donor side. As a donor solution, 1.5 mL of each of the above-described <5-A: phosphate buffer (pH 7.4) suspension liquid of pitavastatin calcium-containing polymer micelles prepared to have a concentration of pitavastatin calcium-containing polymer micelles of 0.5 mass % in terms of pitavastatin calcium> and the above-described <5-C: phosphate buffer (pH 7.4) suspension liquid containing pitavastatin calcium (0.5 mass %)> was applied. As a receptor solution, a phosphate buffer solution (pH 7.4) was used. After 2, 4, 6, 8, 10, and 12 hours, 0.8 mL of the receptor solution was sampled, and 0.8 mL of a fresh receptor solution was supplied. The amount of the drug contained in the sampled receptor solution was measured by HPLC. The relationship between the time from the start of the test to the sampling of the receptor solution and the cumulative amount of the drug permeated is plotted in FIG. 6.

From the results of Test Example 1-6, it was confirmed that the pitavastatin calcium-containing polymer micelles showed high skin permeability also in the three-dimensional skin model as in the case of the tests using the rat abdominal skin (Test Examples 1-2 and 1-3 described above). Further, as can be seen from the results shown in FIG. 6, there is no difference in skin permeability between when the pitavastatin-containing polymer micelles are used and when pitavastatin calcium is applied alone. From the above results, the reason why the pitavastatin-containing polymer micelles exhibited the same or more drug efficacy than pitavastatin calcium used alone in the drug efficacy test using guinea pigs (Test Example 1-4 describe above) is considered to result from the fact that both of them have comparable skin permeability.

Example 2: Effect of Reducing Skin Irritation Caused by Rivastigmine

In Example 2, rivastigmine as a treatment drug for Alzheimer-type dementia was used as a drug to perform tests on skin external preparations obtained by mixing amphiphilic polymer micelles and the drug.

Preparation Example 2-1: Preparation of Drug-free Polymer Micelles 100 mg of $PSar_{65}$-$PLLA_{30}$ obtained in Synthesis Example 1 was dissolved in 40 mL of chloroform, and then the chloroform was distilled off with a rotary evaporator under reduced pressure. After the distillation off under reduced pressure, 10 mL of purified water was added to a thin film formed in a container. Then, the container was immersed in a hot bath at 85° C. for 20 minutes to form micelles, and a filtrate was obtained by filtration using a 0.2 µm PTFE filter and freeze-dried to obtain polymer micelles.

The polymer micelles had an average particle diameter of 35 nm and a drug content of 0, and the collection rate of the polymer micelles was 90% or more.

Preparation Example 2-2: Preparation of Mixture of Polymer Micelles and Drug (1)

Rivastigmine was added to isopropyl myristate (IPM) to prepare a 20 mass % solution (1-A described below). The polymer micelles obtained in Preparation Example 2-1 described above were added to the solution so that the concentration of the polymer micelles was 1 mass % (1-B described below) or 3 mass % (1-C described below) to prepare a suspension liquid in which the polymer micelles were dispersed in the rivastigmine solution.

Preparation Example 2-3: Preparation of Mixture of Polymer Micelles and Drug (2)

The polymer micelles obtained in Preparation Example 2-1 described above were added to oily undiluted rivastigmine (2-A described below) to examine their dispersibility. As a result, when the amount of the polymer micelles added to the undiluted rivastigmine was 10 mass % or less, a suspension liquid was obtained in which the polymer micelles were uniformly dispersed. In this preparation example, the polymer micelles obtained in Preparation Example 2-1 were added to the undiluted rivastigmine so that the concentration of the polymer micelles was 1 mass % (2-B described below), 3 mass % (2-C described below), or 10 mass % (2-D described below) to prepare a suspension liquid in which the polymer micelles were dispersed in the undiluted rivastigmine.

Test Example 2-1: Irritation Test Using Three-Dimensional Skin Model (1)

Figures 1, 7:
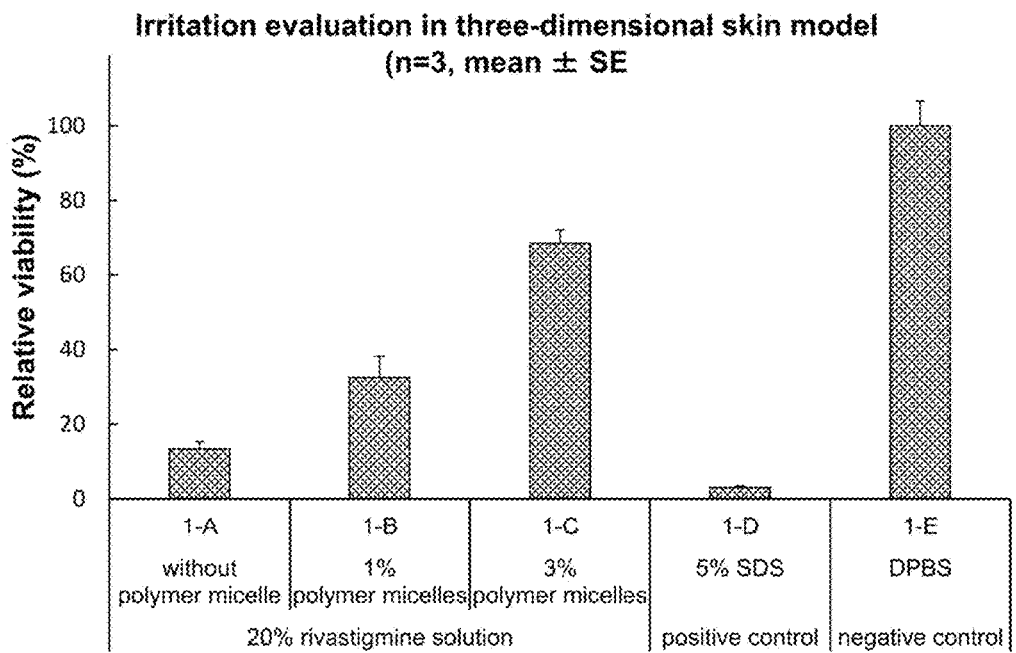
Figures 2, 7:
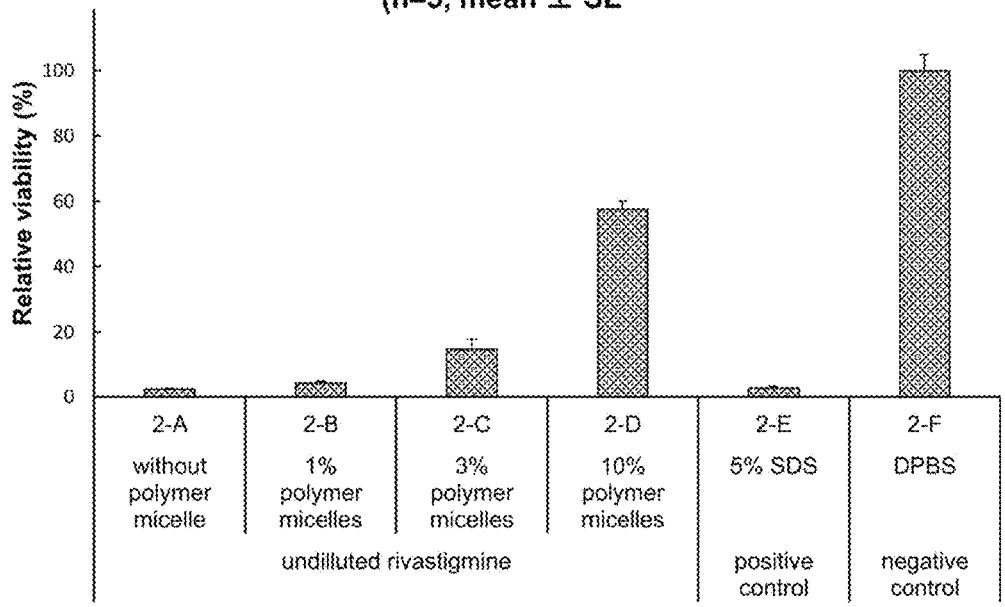

The following <1-A> to <1-E> were used as test materials to perform exposure of the epidermis to the test materials and irritation evaluation in the same manner as in Test Example 1-5 described above using a kit for skin irritation test. FIG. 7-1 shows relative viability compared with a negative control.
<1-A>: 20% Rivastigmine IPM solution
<1-B>: 20% Rivastigmine IPM solution-1% polymer micelle suspension liquid obtained in Preparation Example 2-2
<1-C>: 20% Rivastigmine IPM solution-3% polymer micelle suspension liquid obtained in Preparation Example 2-2
<1-D>: 5% SDS solution; positive control <1-E>: DPBS; negative control Test Example 2-2: Irritation Test Using Three-Dimensional Skin Model (2)

The following <2-A> to <2-F> were used as test materials to perform exposure of the epidermis to the test materials and irritation evaluation in the same manner as in Test Example 1-5 described above using a kit for skin irritation test. FIG. 7-2 shows relative viability compared with a negative control.
<2-A>: Undiluted rivastigmine
<2-B>: Rivastigmine-1% polymer micelle suspension liquid obtained in Preparation Example 2-3
<2-C>: Rivastigmine-3% polymer micelle suspension liquid obtained in Preparation Example 2-3
<2-D>: Rivastigmine-10% polymer micelle suspension liquid obtained in Preparation Example 2-3
<2-E>: 5% SDS solution; positive control
<2-F>: DPBS; negative control As a result of Test Examples 2-1 and 2-2, the relative viability was increased as the amount of the polymer micelles added was increased in both cases where the polymer micelles were added to the rivastigmine solution and where the polymer micelles were added to the undiluted rivastigmine. From these results, it was confirmed that skin irritation caused by the drug was reduced also in the mixture system of the polymer micelles and the drug as in the case where the drug was contained in the polymer micelles (Example 1 described above). That is, it can be seen that when used in combination with the drug, the polymer micelles not encapsulating the drug function as a skin irritation-reducing agent, and therefore a skin external preparation having reduced skin irritation can be obtained by allowing the polymer micelles and the drug to coexist in a mixed state.

Test Example 2-3: Skin Permeation Test Using Three-Dimensional Skin Model

A 20 mass % rivastigmine IPM suspension liquid and a 20 mass % rivastigmine IMP suspension liquid containing 2 mass % of polymer micelles were used as donor solutions to perform a skin permeation test in the same manner as in Test Example 1-6 described above. The skin permeation test was performed by attaching, as a control, a commercially-available skin patch containing rivastigmine as a pharmaceutical component (Exelon Patch 18 mg; 1.3 cm$\phi$ (area: 1.33 cm$^2$), manufactured by Novartis Pharma) to the stratum corneum side of a cultured skin model. The relationship between the time from the start of the test to the sampling of the receptor solution and the cumulative amount of the drug permeated is plotted in FIG. 8.

Figure 8:
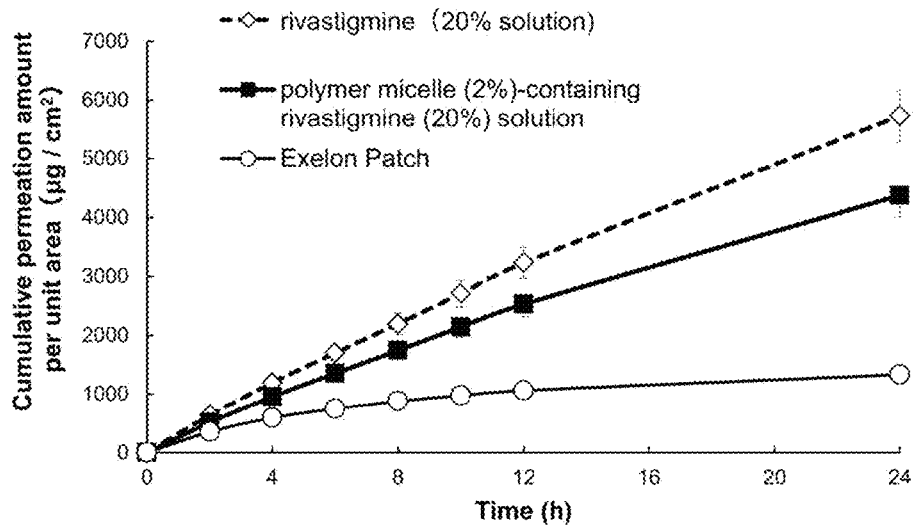
FIG. 8 is a graph showing the results of a permeation test for rivastigmine with the use of a three-dimensional skin model.

From the results shown in FIG. 8, it was confirmed that the polymer micelle-added rivastigmine solution tended to have skin permeability slightly lower than that of the polymer micelle-free rivastigmine solution, but exhibited sufficiently higher skin permeability than the commercially-available skin patch and was therefore useful as a skin external preparation.

Example 3: Effect of Reducing Skin Irritation Caused by Memantine

In Example 3, memantine hydrochloride as a treatment drug for Alzheimer-type dementia was used as a drug to perform a test by applying a skin external preparation obtained by allowing amphiphilic polymer micelles to contain the drug or by applying the drug after the contact of amphiphilic polymer micelles as a skin irritation-reducing agent with the skin.

Preparation Example 3-1: Preparation of Memantine-Containing Polymer Micelles (52 nm)

100 mg of PSar$_{65}$-PLLA$_{30}$ obtained in Synthesis Example 1, and 100 mg of memantine hydrochloride were dissolved in 50 mL of chloroform, and then the chloroform was distilled off with a rotary evaporator under reduced pressure. After the distillation off under reduced pressure, 100 mL of purified water was added to a thin film formed in a container. Then, the container was immersed in a hot bath at 85° C. for 20 minutes to form micelles, and freeze-dried to obtain memantine hydrochloride-containing polymer micelles.

The polymer micelles had an average particle diameter of 52 nm and a drug content of 100 mass %, and the collection rate of the polymer micelles was 90% or more.

Test Example 3-1: Skin Irritation Test Using Three-Dimensional Skin Model

Figure 9:
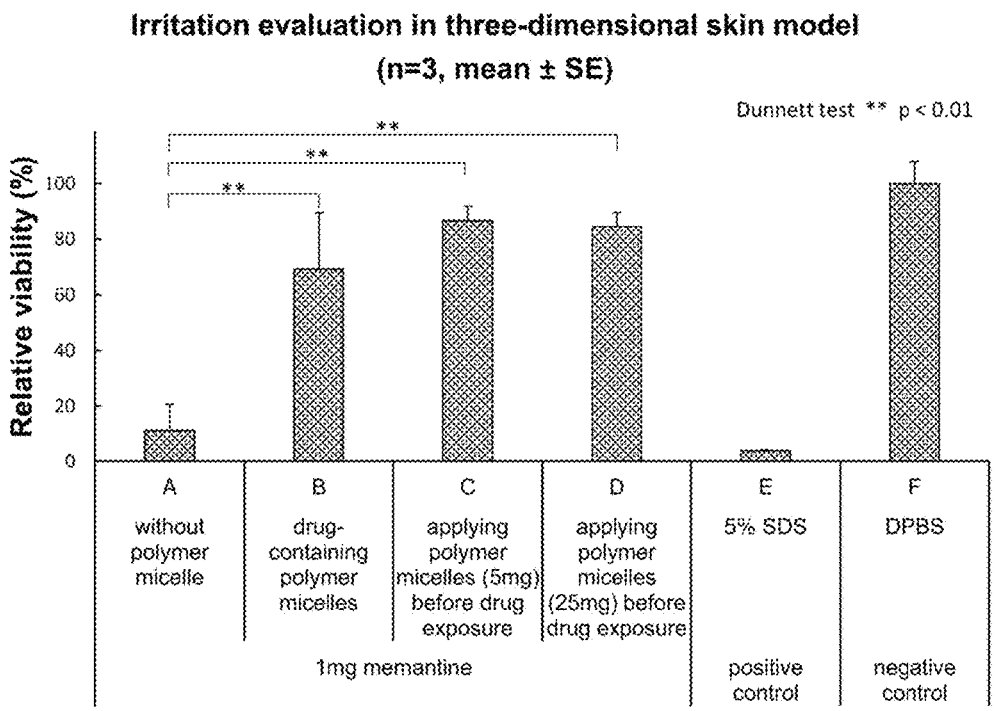
FIG. 9 is a graph showing the results of an irritation test for memantine with the use of a three-dimensional skin model.

A kit for skin irritation test approved by OECD (EPI-200SIT manufactured by KURABO) was used to perform irritation evaluation by exposing the epidermis to test materials according to the following <A> to <E> in the same manner as in Test Example 1-5 described above. FIG. 9 shows relative viability compared with a negative control.
<A>: 25 μL of DPBS was added to the stratum corneum, and immediately after that, 1 mg of memantine hydrochloride (solid) was added to the stratum corneum
<B>: 25 μL of DPBS was added to the stratum corneum, and immediately after that, 2 mg of the drug-containing polymer micelles obtained in Preparation Example 3-1 (equivalent to drug amount of 1 mg) were added to the stratum corneum
<C>: 25 μL of DPBS was added to the stratum corneum, and immediately after that, 5 mg of the drug-free polymer micelles obtained in Preparation Example 2-1 were added to the stratum corneum, and then 1 mg of memantine hydrochloride (solid) was further added to the stratum corneum
<D>: 25 μL of DPBS was added to the stratum corneum, and immediately after that, 25 mg of the drug-free polymer micelles obtained in Preparation Example 2-1 were added to the stratum corneum, and then 1 mg of memantine hydrochloride (solid) was further added to the stratum corneum <E> 5% SDS solution was added to the stratum corneum; positive control <F> DPBS was added to the stratum corneum; negative control As shown in FIG. 9, when the polymer micelles containing memantine as the drug were used <B>, the relative viability was significantly increased as compared to when memantine was used alone <A>. Further, also when memantine was applied after the polymer micelles were applied <C> and <D>, the relative viability was significantly increased as compared to when memantine was used alone <A>. Therefore, it was confirmed that the polymer micelles had the effect of reducing skin irritation. As can be seen from these results, when applied prior to the application of the drug, the polymer micelles function as a skin irritation-reducing agent.

Test Example 3-2: Determination of Amount of IL-1α Produced by ELISA

In the cases of A, B, D, E, and F of Test Example 3-1 described above, a supernatant of the culture medium was sampled after 24 hours from the start of post-incubation, and the amount of IL-1α contained in the supernatant (amount of IL-1α produced) was measured using a commercially-available interleukin (IL)-1α ELISA (Enzyme-Linked Immuno Sorbent Assay) kit. It is to be noted that IL-1α is one of cytokines produced when the skin is irritated. The measurement results are shown together with relative viability in FIG. 10.

Figure 10:
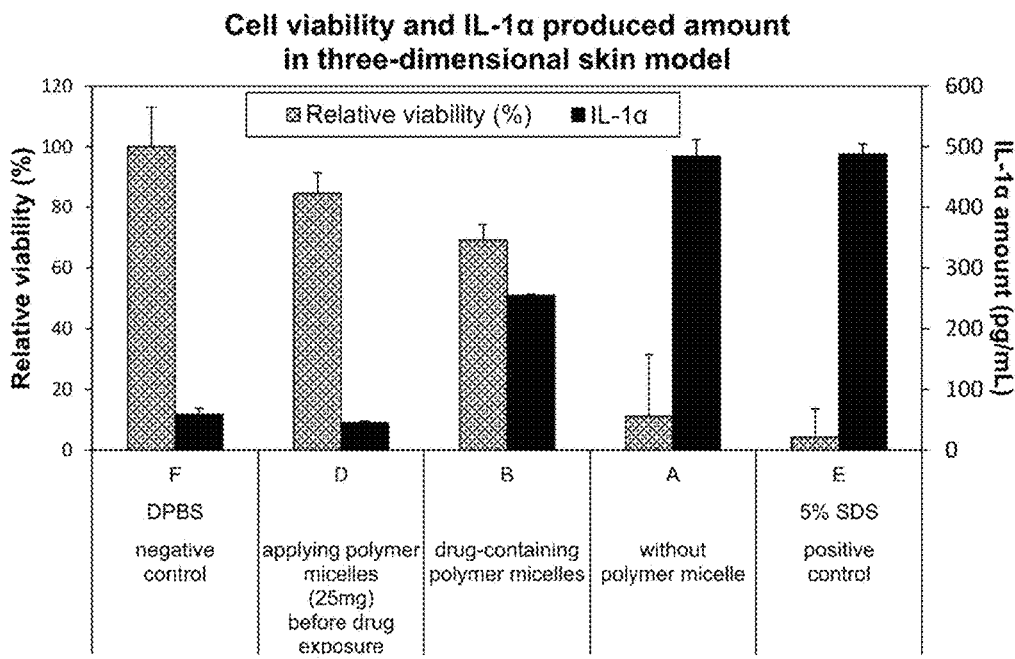
FIG. 10 is a graph showing the results of an irritation test for memantine with the use of a three-dimensional skin model and the measurement results of the amount of IL-1α produced.

As shown in FIG. 10, when the sample achieved a higher relative viability in the irritation test, the amount of IL-1α produced was smaller. From the results, it was confirmed that the use of the polymer micelles was effective at reducing skin irritation also from the viewpoint of the mechanism of skin irritation.

The invention claimed is:

1. A method for reducing skin irritation caused by a drug, comprising:
    administering, to a subject in need of the drug, a skin external preparation comprising the drug, and an amphiphilic block copolymer having a hydrophilic block chain including sarcosine monomer units and a hydrophobic block chain including hydroxy acid monomer units,
    wherein the drug is one of a statin and an Alzheimer-type dementia treatment drug.

2. The method of claim 1, wherein the amphiphilic block copolymer forms a molecular assembly.

3. The method of claim 1, wherein the hydrophilic block chain has 20 or more of sarcosine monomer units.

4. The method of claim 1, wherein the hydrophobic block chain has 10 or more of hydroxy acid monomer units.

5. The method of claim 1, wherein a hydroxy acid of the hydroxy acid-derived structural unit is lactic acid.

6. The method of claim 1, wherein the amphiphilic block copolymer is represented by formula (3),

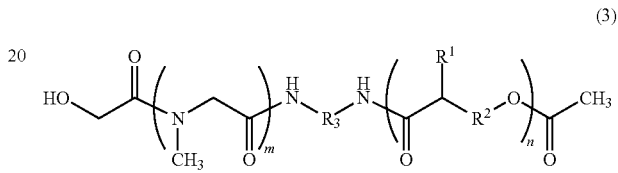

(3)

where R1 is a hydrogen or a methyl group, R2 is a single bond or methylene group, R3 is a divalent hydrocarbon group having 1 to 6 carbons, m is an integer in a range of 20 to 200, and n is an integer in a range of 10 to 100.

7. The method of claim 2, wherein the molecular assembly and the drug coexist in a mixed state.

8. The method of claim 2, wherein a region containing the molecular assembly and a region containing the drug are present in the skin external preparation.

9. The method of claim 6, wherein in the formula (3), m is an integer of 30 to 150, and n is an integer of 15 to 80.

10. The method of claim 1, wherein the molecular assemblies have an average particle diameter in a range of 15 to 60 nm.

11. The method of claim 1, wherein the molecular assemblies have an average particle diameter in a range of 20 to 45 nm.

* * * * *

UNITED STATES PATENT AND TRADEMARK OFFICE
CERTIFICATE OF CORRECTION

PATENT NO. : 10,258,694 B2
APPLICATION NO. : 15/312985
DATED : April 16, 2019
INVENTOR(S) : Kenichi Suzuki et al.

Page 1 of 1

It is certified that error appears in the above-identified patent and that said Letters Patent is hereby corrected as shown below:

In the Claims

Column 24, Lines 12-13, Claim 5:
"The method of claim 1, wherein a hydroxy acid of the hydroxy acid-derived structural unit is lactic acid."
Should read:
--The method of claim 1, wherein a hydroxy acid of the hydroxy acid monomer units is lactic acid.--

Column 24, Lines 38-40, Claim 10:
"The method of claim 1, wherein the molecular assemblies have an average particle diameter in a range of 15 to 60 nm."
Should read:
--The method of claim 1, wherein the amphiphilic block copolymer forms a plurality of molecular assemblies, and the molecular assemblies have an average particle diameter in a range of 15 to 60 nm.--

Column 24, Lines 41-43, Claim 11:
"The method of claim 1, wherein the the molecular assemblies have an average particle diameter in a range of 20 to 45 nm."
Should read:
--The method of claim 1, wherein the amphiphilic block copolymer forms a plurality of molecular assemblies, and the molecular assemblies have an average particle diameter in a range of 20 to 45 nm.--

Signed and Sealed this
Second Day of June, 2020

Andrei Iancu
*Director of the United States Patent and Trademark Office*